(12) United States Patent
Yonezu et al.

(10) Patent No.: US 9,360,448 B2
(45) Date of Patent: Jun. 7, 2016

(54) GAS SENSOR

(75) Inventors: Kunihiko Yonezu, Mie-ken (JP);
Hisaharu Nishio, Tokai (JP); Norimasa Osawa, Inuyama (JP); Tomohiro Tajima, Kasugai (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 195 days.

(21) Appl. No.: 13/560,542

(22) Filed: Jul. 27, 2012

(65) Prior Publication Data
US 2013/0074578 A1 Mar. 28, 2013

(30) Foreign Application Priority Data

Jul. 29, 2011 (JP) .................................. 2011-167328

(51) Int. Cl.
*G01N 27/407* (2006.01)

(52) U.S. Cl.
CPC .......... *G01N 27/4078* (2013.01); *G01N 27/407* (2013.01); *G01N 27/4077* (2013.01); *G01K 2205/04* (2013.01)

(58) Field of Classification Search
CPC .......... G01N 27/4062; G01N 27/4077; G01N 27/407; G01N 27/4075; G01N 33/0054; G01N 27/4078; G01N 33/0037; G01N 1/2252; G01K 2205/04
See application file for complete search history.

(56) References Cited

U.S. PATENT DOCUMENTS

| | | | |
|---|---|---|---|
| 4,364,226 A * | 12/1982 | Croset et al. ..................... 60/276 |
| 5,820,739 A * | 10/1998 | Graser et al. ................... 204/421 |
| 6,068,746 A | 5/2000 | Kojima et al. |
| 7,082,810 B2 * | 8/2006 | Sakamoto et al. ........... 73/24.01 |
| 7,222,516 B2 * | 5/2007 | Nishio et al. .................. 73/23.31 |
| 7,287,413 B2 * | 10/2007 | Nishio et al. .................. 73/23.31 |
| 7,963,145 B2 * | 6/2011 | Hamatani et al. ............. 73/23.31 |
| 8,215,153 B2 * | 7/2012 | Matsubara et al. .......... 73/31.05 |
| 8,702,934 B2 * | 4/2014 | Tsuzuki et al. ............... 204/406 |
| 2007/0199366 A1 * | 8/2007 | Nishio et al. .................. 73/23.31 |
| 2009/0200164 A1 * | 8/2009 | Yoshikawa et al. .......... 204/406 |
| 2011/0174617 A1 | 7/2011 | Tsuzuki et al. |
| 2011/0259084 A1 * | 10/2011 | Atsumi et al. ................ 73/31.05 |
| 2012/0018305 A1 * | 1/2012 | Yoshikawa et al. .......... 204/431 |
| 2012/0055234 A1 * | 3/2012 | Yonezu et al. ................ 73/31.05 |
| 2012/0239271 A1 * | 9/2012 | Tajima et al. ................. 701/102 |

FOREIGN PATENT DOCUMENTS

| | | | |
|---|---|---|---|
| JP | 10-132779 A | 5/1998 | |
| JP | 2001305097 A * | 10/2001 | ........... G01N 27/409 |
| JP | 2010127667 A * | 6/2010 | |
| JP | 2010151792 A * | 7/2010 | |
| JP | 2011022099 A * | 2/2011 | |
| JP | 2011-145270 A | 7/2011 | |

* cited by examiner

*Primary Examiner* — Lisa Caputo
*Assistant Examiner* — Punam Roy
(74) *Attorney, Agent, or Firm* — Sughrue Mion, PLLC

(57) ABSTRACT

A gas sensor (1) includes at least a sensor element (12) which measures the concentration of a specific gas component, a housing (13) which accommodates the sensor element (12), and a base portion (21) which is attached to the housing and is formed of resin. The base portion includes a first base portion (22) which is a portion of the base portion located on the side toward the housing and which is molded integrally with the housing, and a second base portion (23) which is molded separately from the first base portion, which is a portion of the base portion located opposite the housing, and which has a connector portion (23*c*) in which a plurality of terminals (26) electrically connected to the sensor element are disposed such that they extend in a direction intersecting the insertion direction of the sensor element.

4 Claims, 14 Drawing Sheets

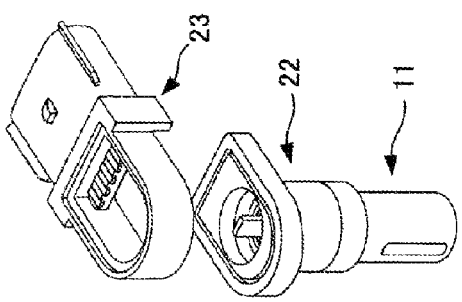
FIG. 4(a) FIG. 4(b) FIG. 4(c) FIG. 4(d)
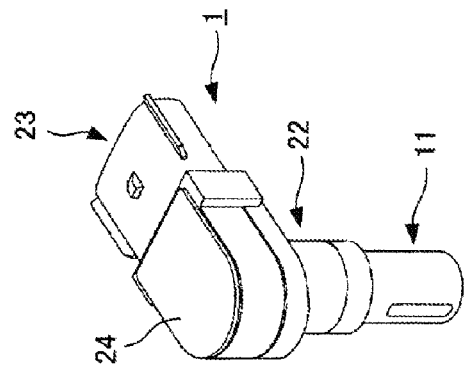
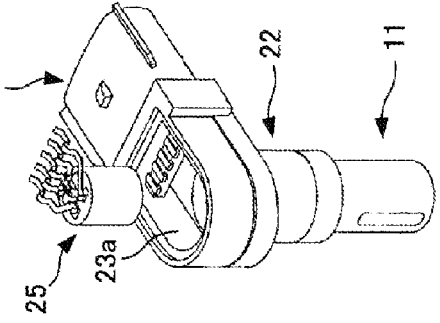
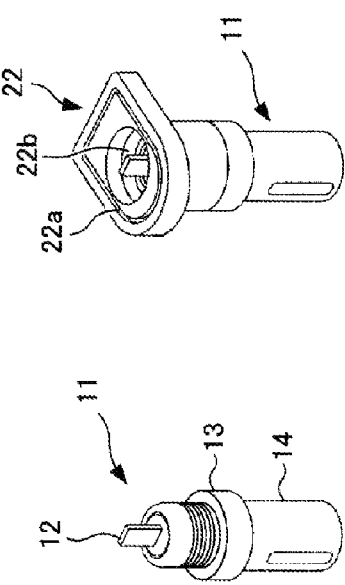
FIG. 4(e) FIG. 4(f) FIG. 4(g)

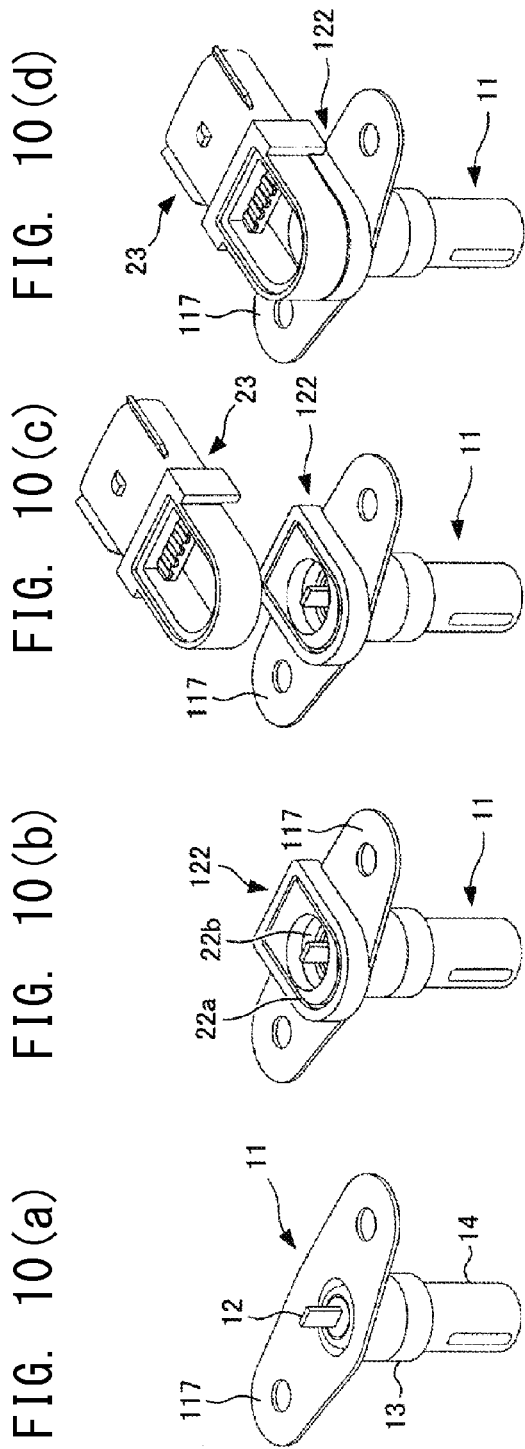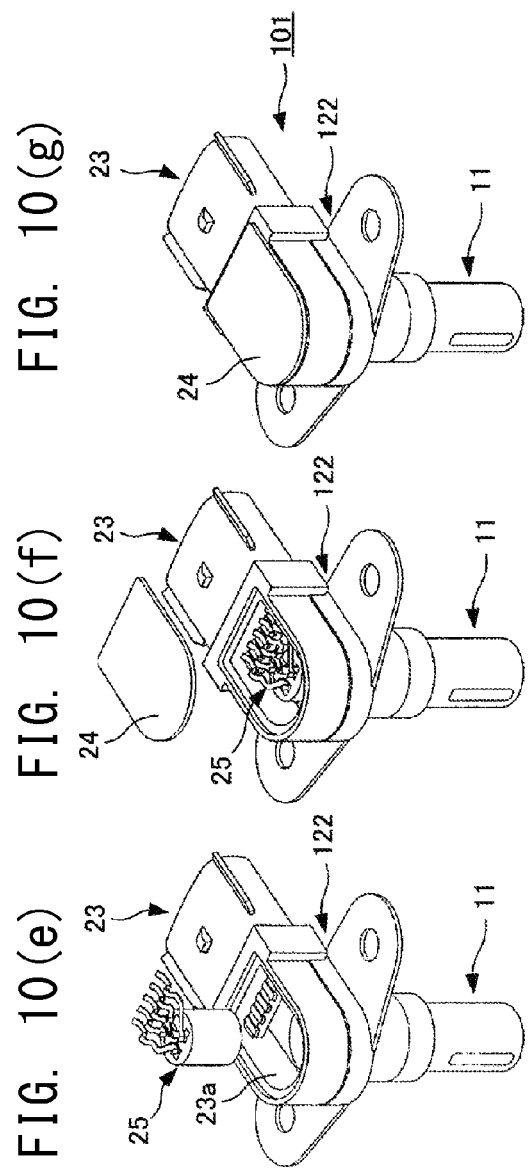

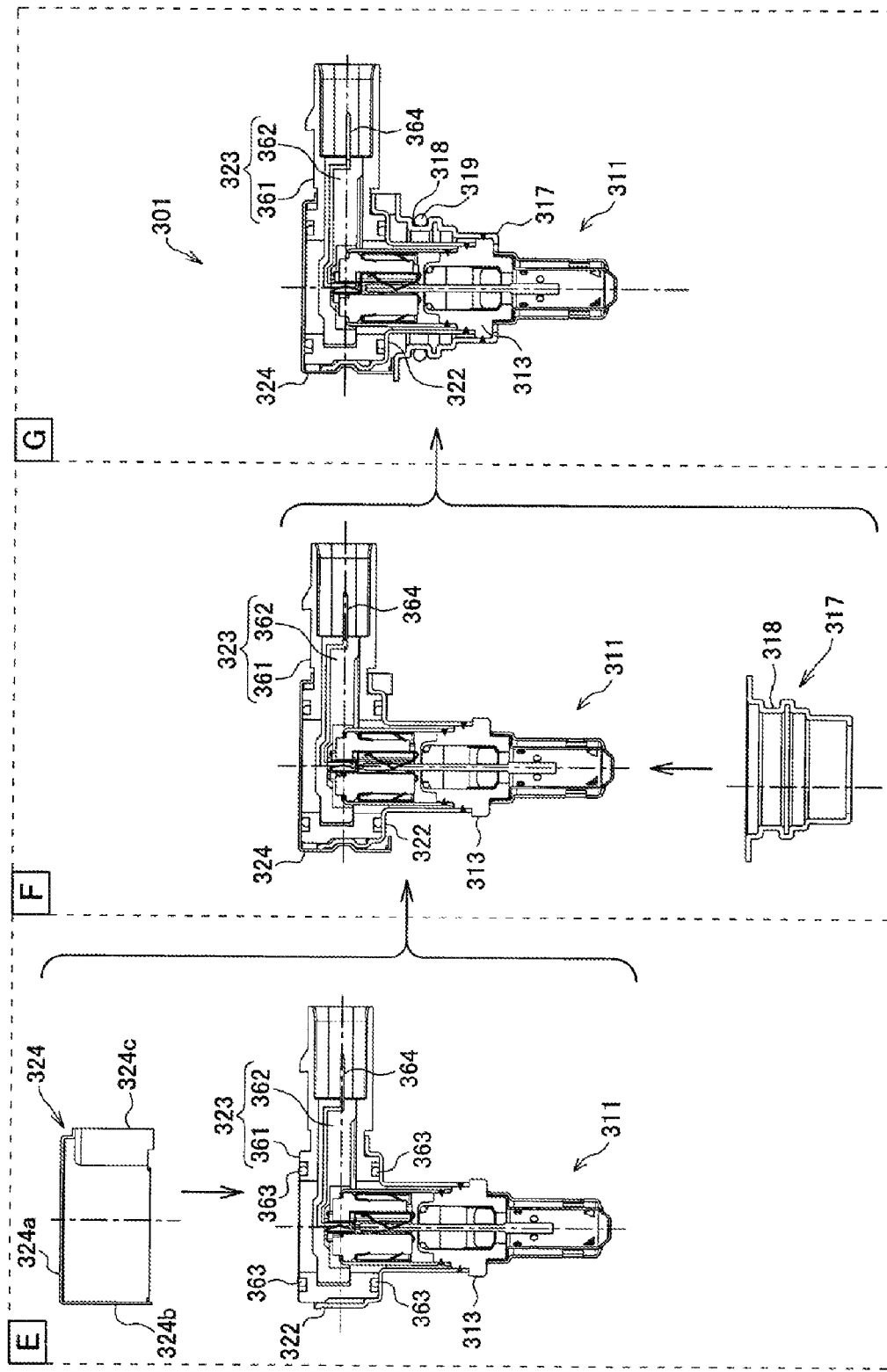

GAS SENSOR

TECHNICAL FIELD

The present invention relates to a gas sensor including a sensor element for measuring the concentration of a gas to be detected.

BACKGROUND ART

In an internal combustion engine, such as a diesel engine or a gasoline engine, in general, an air-fuel ratio (the ratio between air (oxygen) and fuel fed to combustion chambers) is adjusted in order to reduce fuel consumption or purify exhaust gas. In order to control the air-fuel ratio, there is used a measurement signal from a gas sensor which measures the ratio of oxygen contained in intake gas or the ratio of oxygen contained in exhaust gas.

The above-mentioned gas sensor is mainly composed of a sensor element for measuring the concentration of oxygen; a protection cover which covers the circumference of the sensor element; a metallic shell which holds the sensor element; and a base portion which includes a plurality of terminals for leading a measurement signal from the sensor element to an external circuit. Conventionally, the base portion is fabricated by assembling a plurality of thin metal sheets. Therefore, the conventional gas sensor has a problem in that the assembly is troublesome and time consuming.

In order to solve such a problem, there has been proposed a technique of insert-molding a base portion formed of resin integrally or unitarily with a metallic shell, etc. (see, for example, Patent Document 1). By means of forming the base portion from resin to be united with the metallic shell, etc., the work of assembling a plurality of thin metal sheets can be simplified.

PRIOR ART DOCUMENTS

Patent Documents

[Patent Document 1] Japanese Patent Application Laid-Open (kokai) No. H10-132779
[Patent Document 2] Japanese Patent Application Laid-Open (kokai) No. 2011-145270

SUMMARY OF THE INVENTION

Problems to be Solved by the Invention

The gas sensor disclosed in Patent Document 1 has a structure in which the longitudinal direction of the gas sensor coincides with the longitudinal direction of the terminals provided in the base portion (in other words, the direction along which external wiring lines are inserted and removed). Therefore, if the restriction on the installation area around an internal combustion engine is strict, there arises a problem in that the external wiring lines cannot be connected to the base portion of the gas sensor.

A gas sensor which solves such a problem has been also proposed. The proposed gas sensor is configured such that the longitudinal direction of the gas sensor is orthogonal to the longitudinal direction of the terminals provided in the base portion.

However, since the base portion having such a structure is complex in structure as compared with the base portion disclosed in Patent Document 1, the shape of a mold used for insert-molding the base portion tends to become complex.

Also, there has been a problem in that a range in which the position of a communication hole provided in the protection cover can be changed in relation to the longitudinal direction of the terminals is apt to be restricted by the shape of the gas sensor. Moreover, there has been a problem in that, in the case where the base portion formed of resin is insert-molded, a restriction is imposed on the shape of the base portion in order to prevent deformation of the base portion, which deformation would otherwise occur due to, for example, shrinkage of the resin after the molding.

The present invention has been accomplished so as to solve the above-described problems, and an object of the invention is to provide a gas sensor which can increase the degree of freedom in designing the shape of a connector portion formed of resin, can increase the accuracy of the shape, and can facilitate molding.

Means for Solving the Problems

In order to solve the above-described problems, the present invention provides the following means.

A gas sensor of the present invention includes a sensor element which measures the concentration of a specific gas component contained in gas flowing through a flow passage provided in an internal combustion engine, a housing which accommodates the sensor element and which is inserted into the flow passage, and a base portion which is attached to the housing and which is disposed outside the flow passage. The gas sensor being characterized in that the base portion includes a first base portion which is a portion of the base portion located on the side toward the housing; and a second base portion which is molded separately from the first base portion, which is a portion of the base portion located opposite the housing, and which has a connector portion in which a plurality of terminals which are to be connected electrically to the sensor element are disposed such that they extend in a direction intersecting an insertion direction of the sensor element.

According to the gas sensor of the present invention, the base portion is composed of a first base portion which is a housing side portion, and a second base portion having a connector portion. This configuration increases the degree of freedom in designing the shape of the base portion.

Specifically, when the first base portion is molded, the shape of the housing mainly restricts the shape of the first base portion. In the case where the base portion is molded as a single member without dividing it, the shape of the housing and the position and orientation of the plurality of terminals mainly restrict the shape of the first base portion. As compared with such a case, the restriction associated with the molding of the first base portion decreases, and the degree of freedom in designing the shape of the base portion increases. Similarly, when the second base portion is molded, the position and orientation of the plurality of terminals mainly restrict the shape of the second base portion. Therefore, as compared with the case where the base portion is molded as a single member without diving it, the above-mentioned restriction decreases, and the degree of freedom in designing the shape of the base portion increases.

Further, as compared with the case where the base portion is molded as a single member without dividing it, the first base portion and the second base portion can be easily formed in a simple shape, in particular, a shape which is symmetry with respect to an axis or a line. Therefore, it becomes easier to suppress deformation of the first base portion and the second base portion caused by shrinkage of the material after completion of molding.

Since the shapes of the first base portion and the second base portion can be made relatively simple, the shapes of molds used for insert-molding the first base portion and the second base portion can be made simple. Therefore, the manufacturing cost of the molds can be lowered, and the lives of the molds can be extended. As a result, the manufacturing cost of the gas sensor can be lowered.

In the above-described invention, the second base portion may be molded through use of resin.

Through employment of such a configuration, the shapes of molds used for resin-molding the second base portion can be simplified. Therefore, the manufacturing cost of the molds can be lowered, and the lives of the molds can be extended. As a result, the manufacturing cost of the gas sensor can be lowered.

In the above-described invention, desirably, the second base portion has a through-hole for accommodating a relay portion which electrically connects the sensor element and the plurality of terminals; the plurality of terminals are molded integrally with the second base portion in a state in which the terminals are united by the connection portion at their end portions on the side toward the relay portion and in a state in which the end portions on the side toward the relay portion project toward the interior of the through-hole; and subsequently, the connection portion is cut from the plurality of terminals projecting from the wall surface of the through-hole toward the interior thereof, whereby the plurality of terminals are disposed inside the second base portion.

Also, since the end portions of the plurality of terminals on the relay portion side project inward from the wall surface of the through-hole, it becomes easier to suppress deterioration of the accuracy in positioning the terminals in relation to one another. Specifically, the required operation is merely disposing the plurality of terminals, which is united by the connection portion, in the molds. Therefore, as compared with the case where the plurality of terminals are disposed one by one in the molds, it becomes easier to suppress deterioration of the accuracy in positioning the terminals. Also, the work required for disposing the plurality of terminals can be eliminated.

Also, since the connection portion and the relay-portion-side end portions of the plurality of terminals project toward the interior of the through-hole of the second base portion, the connection portion can be readily separated from the terminals. Namely, since a pair of cutting tools for separating the connection portion from the terminals can be inserted into the through-hole through the opposite openings thereof, the operation of nipping and cutting the portions between the connection portion and the terminals is easy as compared with the case where the connection portion projects toward the interior of a hole which is closed at one end thereof.

Notably, the end portions of the plurality of terminals on the side opposite the relay portion are disposed to project into the interior of the connector portion, and can be electrically connected to external wiring.

In the above-described invention, desirably, the first base portion includes a lower part which is a portion on the side toward the housing and which extends in a direction in which the housing extends, and a plate-shaped upper part which is a portion on the side toward the second base portion and which extends in a direction in which the plurality of terminals extend; and a concave portion is formed on a surface of the upper part located on the side toward the housing.

By means of forming a concave portion in the upper part of the first base portion, the amount of the material used for forming the first base portion can be reduced without deteriorating the shape accuracy of the base portion. At the same time, the weight of the gas sensor can be reduced. That is, since a connector portion which greatly impairs axis symmetry or plane symmetry is not provided on the first base portion, the shrinkage of the material after completion of molding is less likely to cause deformation of the first base portion. In particular, even when the concave portion is provided at a position where the concave portion overlaps the connector portion of the base portion, the first base portion hardly deforms. Therefore, the concave portion can be easily provided.

In the above-described invention, desirably, the housing further includes a plate-shaped flange portion which extends outward from the outer circumference of the housing in the radial direction; and the first base portion is molded integrally with the housing and the flange portion through use of first and second molds whose parting plane coincides with the flange portion.

In the case where the flange portion is provided as described above, the first base portion is molded integrally with the housing and the flange portion through use of a first mold and a second mold, the parting plane of which coincides with the flange portion. In the case where a restriction is imposed on the position of the parting plane of the molds, the gas sensor of the present invention can simplify the shape of the molds as compared with the case where the base portion is molded as a single member without dividing it, because the connector portion is not provided on the first base portion which is molded integrally with the flange portion.

Effect of the Invention

According to the gas sensor of the present invention, the base portion is composed of the first base portion which is a housing side portion, and the second base portion having the connector portion. This configuration increases the degree of freedom in designing the shape of the base portion. Also, the shapes of the first base portion and the second base portion can be made simple as compared with the case where the base portion is molded as a single member without dividing it. Therefore, it is possible to suppress deformation of the first base portion and the second base portion caused by shrinkage of the material after completion of molding. Moreover, the shapes of molds used for molding the first base portion and the second base portion can be made simple. Therefore, the manufacturing cost of the molds can be lowered, and the lives of the molds can be extended. As a result, the molding of the gas sensor can be facilitated.

BRIEF DESCRIPTION OF THE DRAWINGS

FIGS. 4(*a*) to 4(*g*) Perspective views showing the steps of assembling the oxygen sensor of FIG. 1.

FIGS. 10(a) to 10(g) Perspective views showing the steps of assembling the oxygen sensor of FIG. 8.

FIG. 15 Explanatory views showing steps E to G of the steps of assembling the oxygen sensor of FIG. 13.

MODE FOR CARRYING OUT THE INVENTION

[First Embodiment]

Figure 1:
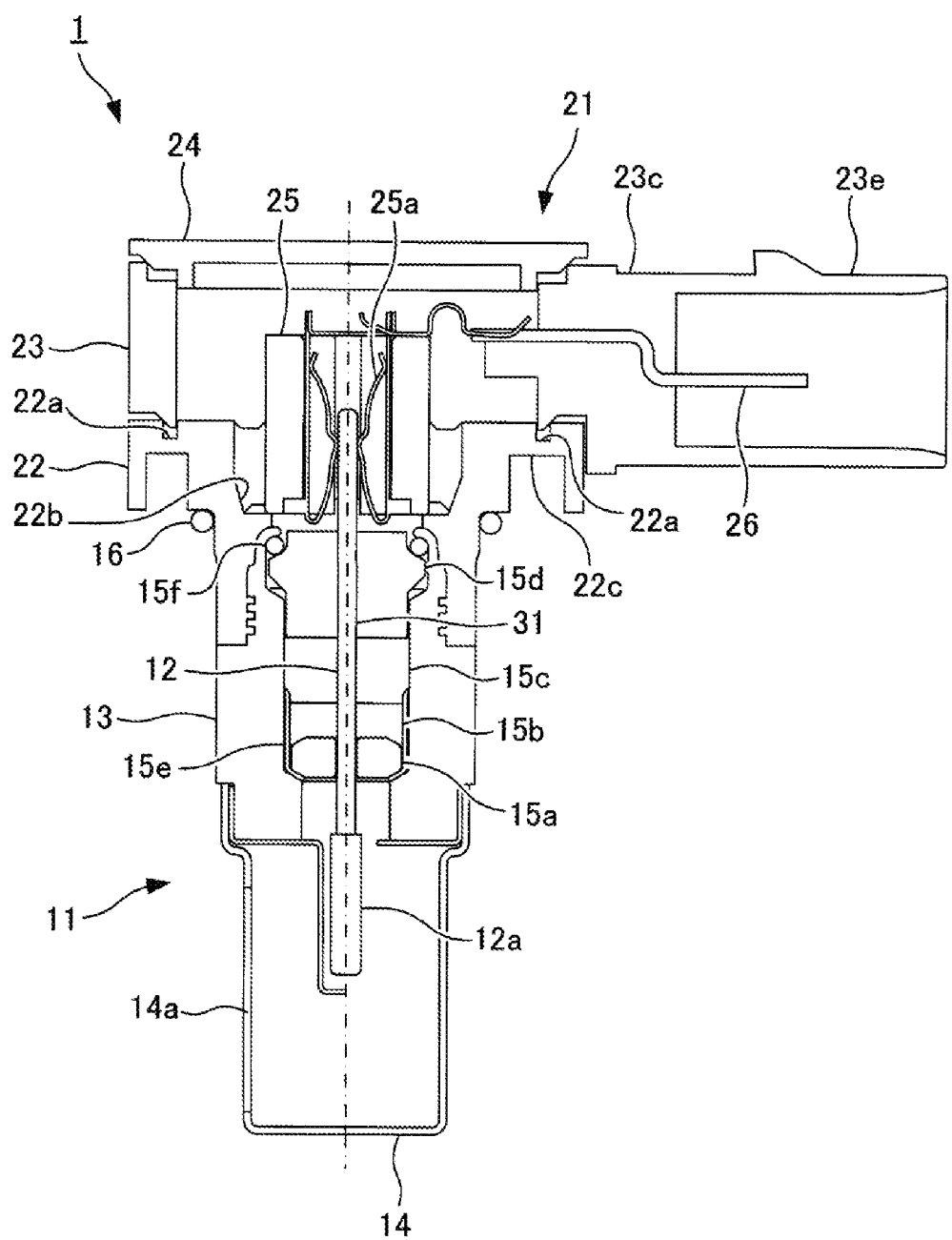
FIG. 1 Sectional view schematically showing the structure of an oxygen sensor according to a first embodiment of the present invention.

An oxygen sensor 1 according to a first embodiment of the present invention will now be described with reference to FIGS. 1 to 7. FIG. 1 is a sectional view schematically showing the structure of the oxygen sensor 1 according to the first embodiment.

The oxygen sensor (gas sensor) 1 of the present embodiment is applied to an engine (internal combustion engine) which serves as a power source of a vehicle such as an automobile. More specifically, the oxygen sensor 1 is adapted to measure the concentration of oxygen, which is a specific gas component contained in gas taken into the engine. As shown in FIG. 1, the oxygen sensor 1 is mainly composed of an element assembly 11 including a sensor element 12, and a base portion 21.

The greater part of the element assembly 11 is inserted into an intake pipe (flow passage), and the sensor element 12 adapted to measure the oxygen concentration of intake gas is accommodated therein. As shown in FIG. 1, the element assembly 11 is mainly composed of the sensor element 12; a metallic shell (housing) 13 which accommodates and holds the sensor element 12; an external protector (housing) 14; a ceramic ring 15a; a first talc ring 15b; a second talc ring 15c; and a sleeve 15d.

The sensor element 12 is a measurement section for measuring the oxygen concentration of intake gas flowing through the intake pipe. The sensor element 12 is formed by laminating or stacking successively a pump cell, an insulation layer having a hollow measurement chamber, an electromotive force cell, a reinforcing plate, and a heater 31 to be described.

The pump cell is mainly formed of partially stabilized zirconia ($ZrO_2$), which is an oxygen-ion conductive solid electrolyte, and porous electrodes mainly formed of platinum are provided on the front and back surfaces thereof. Like the pump cell, the electromotive force cell is formed of partially stabilized zirconia ($ZrO_2$), which is an oxygen-ion conductive solid electrolyte. Porous electrodes mainly formed of platinum are provided on the front and back surfaces of the electromotive force cell.

One of the paired porous electrodes provided on the pump cell and one of the paired porous electrodes provided on the electromotive force cell are disposed to face the measurement chamber, communicate with each other to have the same potential, and are connected to a single electrode terminal formed on the surface of a rear end portion of the sensor element 12. The porous electrode disposed on the side of the pump cell opposite the measurement chamber and the porous electrode disposed on the side of the electromotive force cell opposite the measurement chamber are connected to two electrode terminals formed on the surface of the rear end portion of the sensor element 12.

The reinforcing plate is stacked on the electromotive force cell such that it covers the porous electrode provided on the side of the electromotive force cell opposite the measurement chamber and forms a reference oxygen chamber within the porous electrode. As described above, the insulation layer having the measurement chamber formed therein intervenes between the pump cell and the electromotive force cell. The measurement chamber communicates with an external gas atmosphere; i.e., intake gas flowing through the intake pipe, via a porous diffusion layer separately provided in the insulation layer.

A detection portion 12a through which a current corresponding to the oxygen concentration flows is formed at the forward end (the lower end in FIG. 1) of the sensor element 12, and the above-described three electrode terminals and two terminals for supplying electric power to the heater 31 are provided at the rear end (the upper end in FIG. 1) of the sensor element 12. In the sensor element 12, the flow direction and magnitude of the current flowing through the oxygen pump cell are controlled such that a constant electromotive force (inter-electrode voltage) is generated in the electromotive force cell. Notably, a portion of the oxygen pump cell at which the porous electrodes are disposed corresponds to the above-mentioned detection portion 12a.

The heater 31 is stacked on the reinforcing plate, and is united together with the pump cell, the electromotive force cell, and the reinforcing plate. The heater 31 includes a heater resistor which is formed of a conductor and is sandwiched between a pair of alumina sheets. One end of the heater 31 is connected to a DC power supply (e.g., a battery having an output voltage of 12 V), and the other end of the heater 31 is connected to a heater control circuit (not illustrated). When the heater 31 generates heat as a result of the heater control circuit being driven, the temperatures of the pump cell and the electromotive force cell increase so that these cells become active. Thus, the detection of gas (oxygen concentration) by the sensor element 12 becomes possible.

The metallic shell 13 is formed from a metal (e.g., stainless steel) into a tubular shape, and has a wall thickness greater than that of the external protector 14. The ceramic ring 15a, the first talc ring 15b, the second talc ring 15c, the sleeve 15d, the sensor element 12, etc. are accommodated in the metallic shell 13.

A portion of the metallic shell 13 on the forward end side (lower side in FIG. 1) has an outer diameter smaller than that of a central portion thereof, and the external protector 14 is attached to the diameter-reduced portion. Meanwhile, a portion of the metallic shell 13 on the rear end side (upper side in FIG. 1) has an outer diameter smaller than that of the central portion thereof, and annular grooves 13a are formed on the outer circumferential surface of the diameter-reduced portion (see FIG. 2). When a lower base portion 22 to be described later is insert-molded integrally with the metallic shell 13, the resin which constitutes the lower base portion 22 flows into the grooves 13a.

The external protector 14 is a metal member formed into the shape of a cylindrical tube which is closed at one end thereof. The external protector 14 accommodates the detection portion 12a of the sensor element 12, and protects the detection portion 12a. The external protector 14 is welded to the metallic shell 13 in a state in which a forward end portion of the metallic shell 13 is inserted into the opening of the cylindrical external protector 14.

A gas introduction hole 14a is provided in the circumferential wall of the external protector 14. The gas introduction hole 14a introduces the intake gas flowing through the intake pipe into the space inside the external protector 14, and introduces the intake gas to a region around the detection portion 12a of the sensor element 12. In the present embodiment, the gas introduction hole 14a is a rectangular through-hole extending in the direction of the center axis of the cylindrical external protector 14 (the vertical direction of FIG. 1). When the oxygen sensor 1 is installed, the gas introduction hole 14a is disposed such that it is open toward the downstream side with respect to the gas flow direction within the intake pipe.

The ceramic ring 15a is a cylindrical member formed of alumina ($Al_2O_3$), and the sensor element 12 extends therethrough. The first talc ring 15b and the second talc ring 15c are cylindrical members formed by compressing talc powder, and the sensor element 12 extends therethrough.

The ceramic ring 15a, the first talc ring 15b, the second talc ring 15c are disposed such that the ceramic ring 15a, the first talc ring 15b, the second talc ring 15c are arranged in this sequence from the forward end of the sensor element 12 toward the rear end thereof. The entire ceramic ring 15a, the entire first talc ring 15b, and a lower portion of the second talc ring 15c are accommodated in a metal cup 15e formed into the shape of a cylindrical tube which is closed at one end thereof. The metal cup 15e is disposed between the inner circumferential surface of the metallic shell 13 and the outer circumferential surfaces of the ceramic ring 15a and the first talc ring 15b. Notably, a through-hole through which the sensor element 12 is passed is formed in the closed end of the metal cup 15e.

The sleeve 15d is a cylindrical member disposed rearward of the second talc ring 15c, and presses the ceramic ring 15a, the first talc ring 15b, and the second talc ring 15c toward the forward end of the sensor element 12 in cooperation with the metallic shell 13. An annular packing 15f is disposed between the rear end (upper end in FIG. 2) of the sleeve 15d and the metallic shell 13. The packing 15f prevents application of an unbalanced load onto the sleeve 15d when the rear end of the metallic shell 13 is deformed inward in the radial direction and crimped.

Next, the base portion 21, which is the characteristic portion of the oxygen sensor 1 of the present embodiment, will be described.

The base portion 21 is a portion which is disposed outside the intake pipe and which is formed of resin, which is excellent in formability as compared with other materials such as metal. As shown in FIG. 1, the base portion 21 is mainly composed of a lower base portion (first base portion) 22, an upper base portion (second base portion) 23, and a cap portion 24. A separator (relay portion) 25 for establishing electrical communication between a plurality of terminals 26 to be described later and the sensor element 12 is disposed inside the base portion 21. In the present embodiment, both the lower base portion 22 and the upper base portion 23 are formed of polyphenylene sulfide resin.

The lower base portion 22 and the upper base portion 23 are components which are separately insert-molded and are combined so as to constitute the base portion 21.

Figure 2:
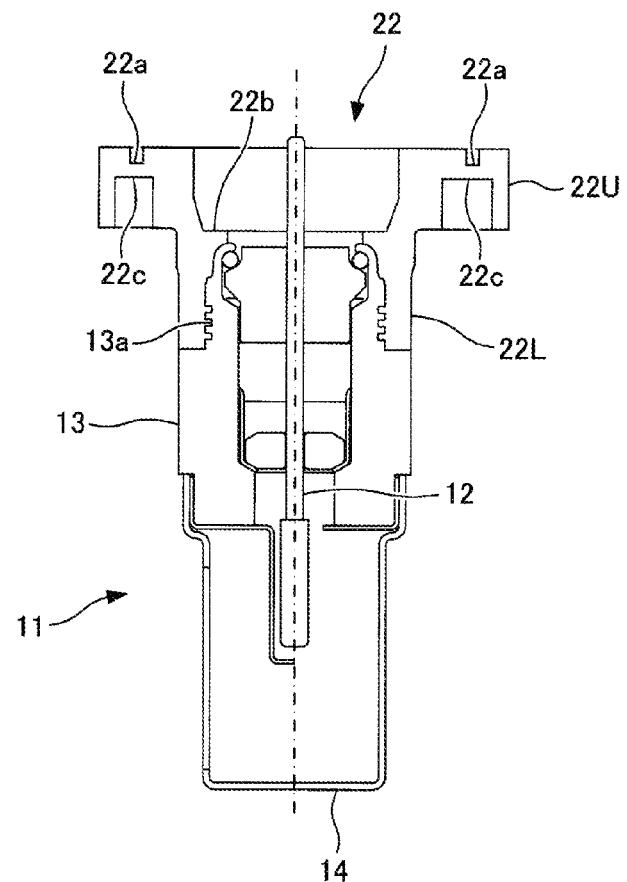
FIG. 2 Partial sectional view showing the structure of a lower base portion of FIG. 1.

The lower base portion 22, which constitutes a portion (a lower portion in FIG. 1) of the base portion 21 located on the side toward the metallic shell 13 and the sensor element 12, is a component which is insert-molded unitarily with the metallic shell 13. As shown in FIG. 2, which is a partial sectional view showing the structure of the lower base portion 22, a lower part 22L of the lower base portion 22 has the form of a circular column having an outer diameter approximately equal to that of a central portion of the metallic shell 13; and an upper part 22U of the lower base portion 22 has the form of a plate projecting outward from the lower part 22L in the radial direction.

A combining groove 22a, a separator hole 22b, and a recess (concave portion) 22c are mainly provided on the upper part 22U of the lower base portion 22.

The combining groove 22a is a concave portion formed on the upper surface of the upper part 22U (the surface which comes into contact with the upper base portion 23). When the lower base portion 22 and the upper base portion 23 are combined together, a combining protrusion 23b provided on the upper base portion 23 is fitted into the combining groove 22a. The combining groove 22a is an annular groove continuously surrounding the separator hole 22b, and prevents entry of water or the like into the space where the separator 25 is disposed, in cooperation with the combining protrusion 23b fitted into and welded to the combining groove 22a.

The separator hole 22b extends from the upper surface of the upper part 22U toward the metallic shell 13, and forms the space where the separator 25 is disposed, in cooperation with a through-hole 23a of the upper base portion 23 and the cap portion 24. The upper ends of the metallic shell 13 and the sleeve 15d are exposed to a bottom portion of the separator hole 22b, and the rear end of the sensor element 12 extends from the bottom portion of the separator hole 22b to an inner portion of the separator hole 22b.

The recess 22c is a concave portion which is provided on the lower surface of the upper part 22U so as to reduce the amount of resin used for the lower base portion 22 and decrease the weight of the oxygen sensor 1. In the present embodiment, the recess 22c is an annular groove which circumferentially surrounds the lower part 22L. However, the recess 22c is not limited to the annular groove, and may be a set of separated arcuate grooves or a recess having any of other various shapes. No particular limitation is imposed on the shape of the recess 22c.

As shown in FIG. 1, an O-ring 16 for maintaining airtightness between the intake pipe and the oxygen sensor 1 is provided at a step portion which is the boundary between the lower part 22L and the upper part 22U of the lower base portion 22.

The O-ring 16 is a ring-shaped member which is formed of a resin having elasticity such as rubber, and has a circular cross section. The inner peripheral end of the O-ring 16 is in contact with the lower part 22L of the lower base portion 22, and the upper end of the O-ring 16 is in contact with the upper part 22U of the lower base portion 22. Also, the outer peripheral end of the O-ring 16 is in contact with the wall surface of a through-hole which is provided in the intake pipe and into which the oxygen sensor 1 is inserted.

Figure 3:
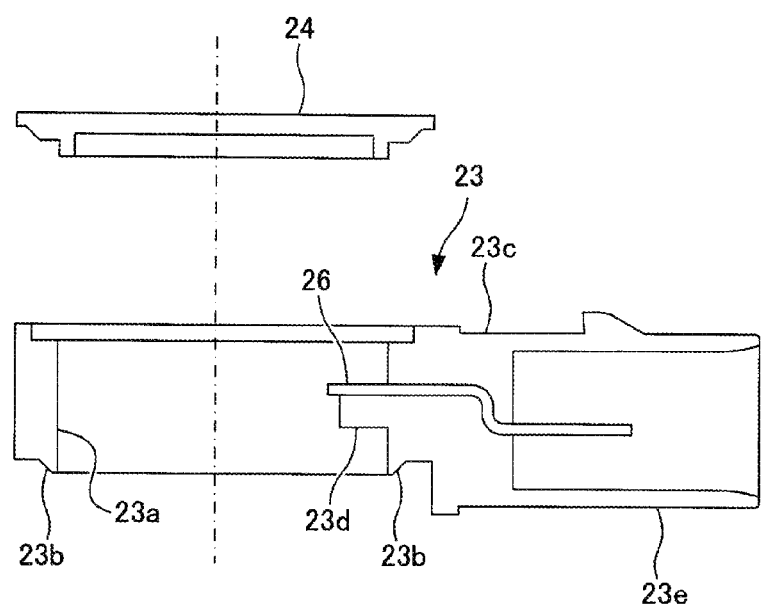
FIG. 3 Partial sectional view showing the structure of an upper base portion of FIG. 1.

The upper base portion 23 constitutes a portion (an upper portion in FIG. 1) of the base portion 21 which is located away from the metallic shell 13 and the sensor element 12. The upper base portion 23 is a component which extends in a direction (the left-right direction in FIG. 1) intersecting (more preferably, perpendicular to) the insertion direction of the oxygen sensor 1 (the vertical direction in FIG. 1). As shown in FIG. 3, which is a partial sectional view showing the structure of the upper base portion 23, the through-hole 23a, the combining protrusion 23b, and a connector portion 23c are mainly provided on the upper base portion 23.

The through-hole 23a is a hole which is formed in a part of the upper base portion 23, which part faces the lower base portion 22, such that the hole extends through that part in the insertion direction of the oxygen sensor 1; i.e., in a direction in which the sensor element 12 extends. A ledge portion 23d is provided on a portion of the wall surface of the through-hole 23a, which portion is located adjacent to the connector portion 23c, such that the ledge portion 23d projects from the wall surface toward an inner or central portion (hereinafter referred to as the "interior") of the through-hole 23a. The plurality of terminals 26 to be described later are disposed on the upper surface of the ledge portion 23d.

The combing protrusion 23b is a ridge which projects from the surface of the upper base portion 23 facing the lower base portion 22 and which surrounds the circumference of the through-hole 23a. The part of the upper base portion 23 facing the lower base portion 22; i.e., the part of the upper base portion 23 where the through-hole 23a and the combining protrusion 23b are provided, is smaller in a dimension in the insertion direction of the oxygen sensor 1 (i.e., the thickness of the upper base portion 23) as compared with a portion where the connector portion 23c is provided.

The connector portion 23c serves as a connection portion through which a measurement signal from the sensor element 12 is output to a control section (not shown) disposed externally of the oxygen sensor 1, and through which electric power supplied to the heater 31 is input. The plurality of terminals 26 and a tubular portion 23e which extends to surround the terminals 26 are mainly provided on the connector portion 23c. The terminals 26 are electrically connected to the sensor element 12 and the heater 31 through the separator 25.

The plurality of terminals 26 are rod-like members (e.g., members formed into the shape of flat rods) formed of a metal having a high electrical conductivity. The terminals 26 are disposed such that they extend in a direction (the left-right direction in FIG. 1) intersecting (more preferably, perpendicular to) the insertion direction of the oxygen sensor 1, and their first end portions project into the through-hole 23a and their second end portions project into the interior space of the tubular portion 23e. The plurality of terminals 26, which extend parallel to one another, are arranged in a row at predetermined intervals.

In the present embodiment, one terminal 26 is provided for each of the three electrode terminals of the sensor element 12 and the two terminals of the heater 31; i.e., five terminals 26 are provided in total. These terminals 26 are bent in a crank shape.

The tubular portion 23e is a portion which extends in parallel to the plurality of terminals 26 disposed therein and into which an external connector connected to the control section is inserted. The tubular portion 23e is adapted to hold the inserted external connector and prevent the external connector from coming off at an unintended timing.

The cap portion 24 is a plate-like component, and is disposed in a region of the upper surface of the upper base portion 23 where the through-hole 23a is formed. The cap portion 24 closes the space in which the rear end of the sensor element 12 and the separator 25 are disposed, to thereby prevent entry of water or the like into that space.

Notably, instead of using the cap portion 24, entry of water or the like into the space in which the rear end of the sensor element 12 and the separator 25 are disposed may be prevented by a different method such as resin potting (i.e., the space is filled with resin). No particular limitation is imposed on the method of preventing entry of water or the like.

As shown in FIG. 1, the separator (relay portion) 25 is a cylindrical component formed of an insulating ceramic. Five conduction members 25a for establishing electrical conduction with the sensor element 12 are disposed inside the separator 25, and a rear end portion of the sensor element 12 is inserted into the separator 25. When the rear end portion of the sensor element 12 is inserted into the separator 25, the five electrode terminals of the sensor element 12 come into electrical contact with the five conduction members 25a. Also, the five conduction members 25a can be electrically connected to the five terminals 26 of the connector portion 23c.

Here, the steps of assembling the oxygen sensor 1 will be briefly described with reference to FIGS. 4(a) to 4(g), which are perspective views showing the steps of assembling the oxygen sensor 1.

First, as shown in FIG. 4(a), an element assembly 11, which is composed of the sensor element 12, the metallic shell 13, the external protector 14, the ceramic ring 15a, the first talc ring 15b, the second talc ring 15c, and the sleeve 15d, is prepared (see FIG. 1).

Figure 5:
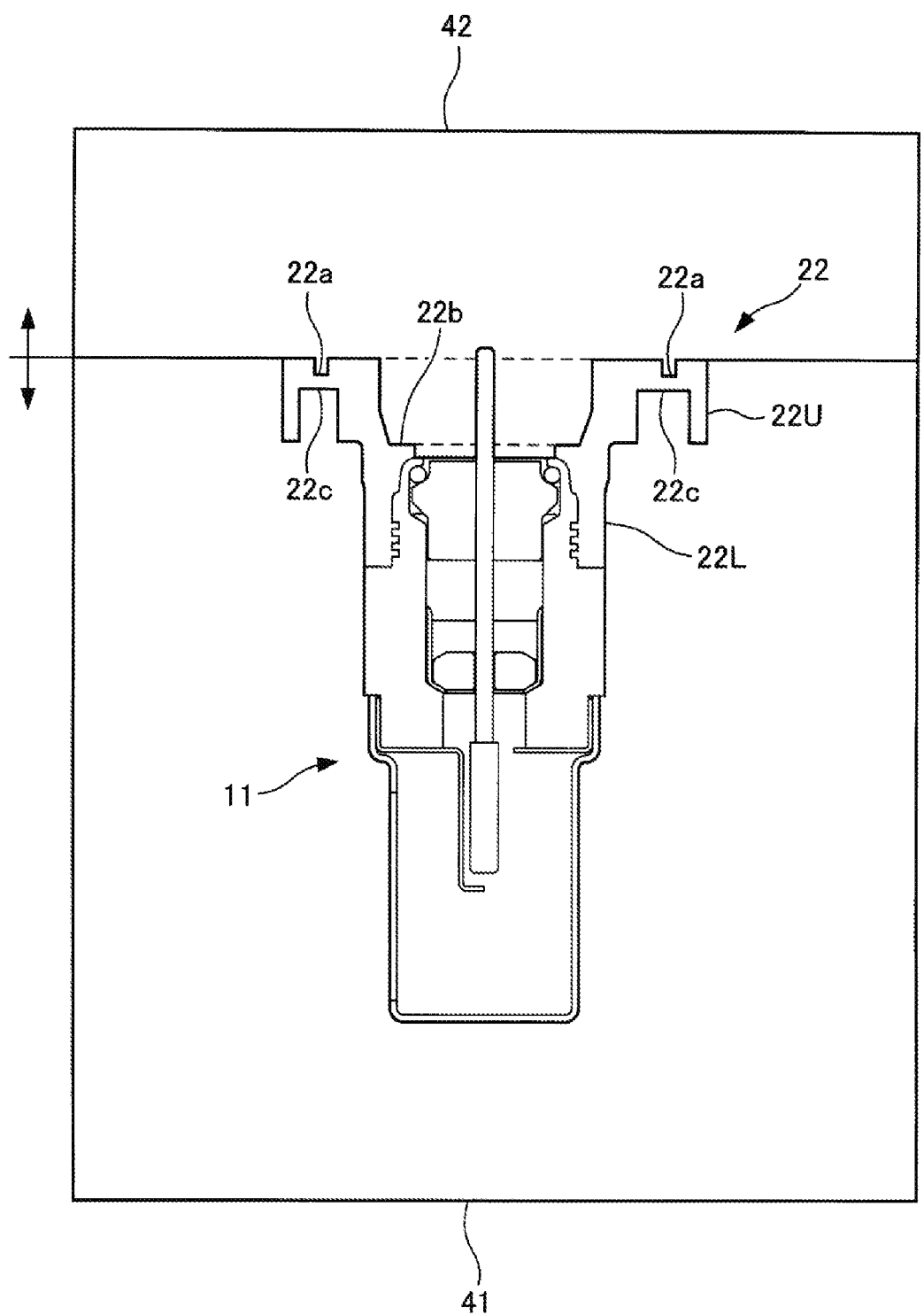
FIG. 5 Sectional view showing molds for insert molding the lower base portion of FIG. 2.

Subsequently, as shown in FIG. 4(b), the lower base portion 22 is insert-molded on the element assembly 11. As shown in FIG. 5, which is a sectional view showing the insert molding of the lower base portion 22, the insert molding is performed through use of a first lower portion mold 41 and a second lower portion mold 42. The first lower portion mold 41 has a convex shape formed thereon which corresponds to the element assembly 11, the lower part 22L of the lower base portion 22, and the lower and side surfaces of the upper part 22U of the lower base portion 22. The second lower portion mold 42 has a profile having a projection(s) and a depression(s) (hereinafter referred to as an "uneven profile") formed thereon which corresponds to the upper surface of the upper part 22U of the lower base portion 22. More specifically, concaves and convexes corresponding to the combing groove 22a, the separator hole 22b, etc. are formed. Notably, arrows provided on the left side of the first lower portion mold 41 and the second lower portion mold 42 in FIG. 5 show a parting plane between the first lower portion mold 41 and the second lower portion mold 42.

Figure 6:
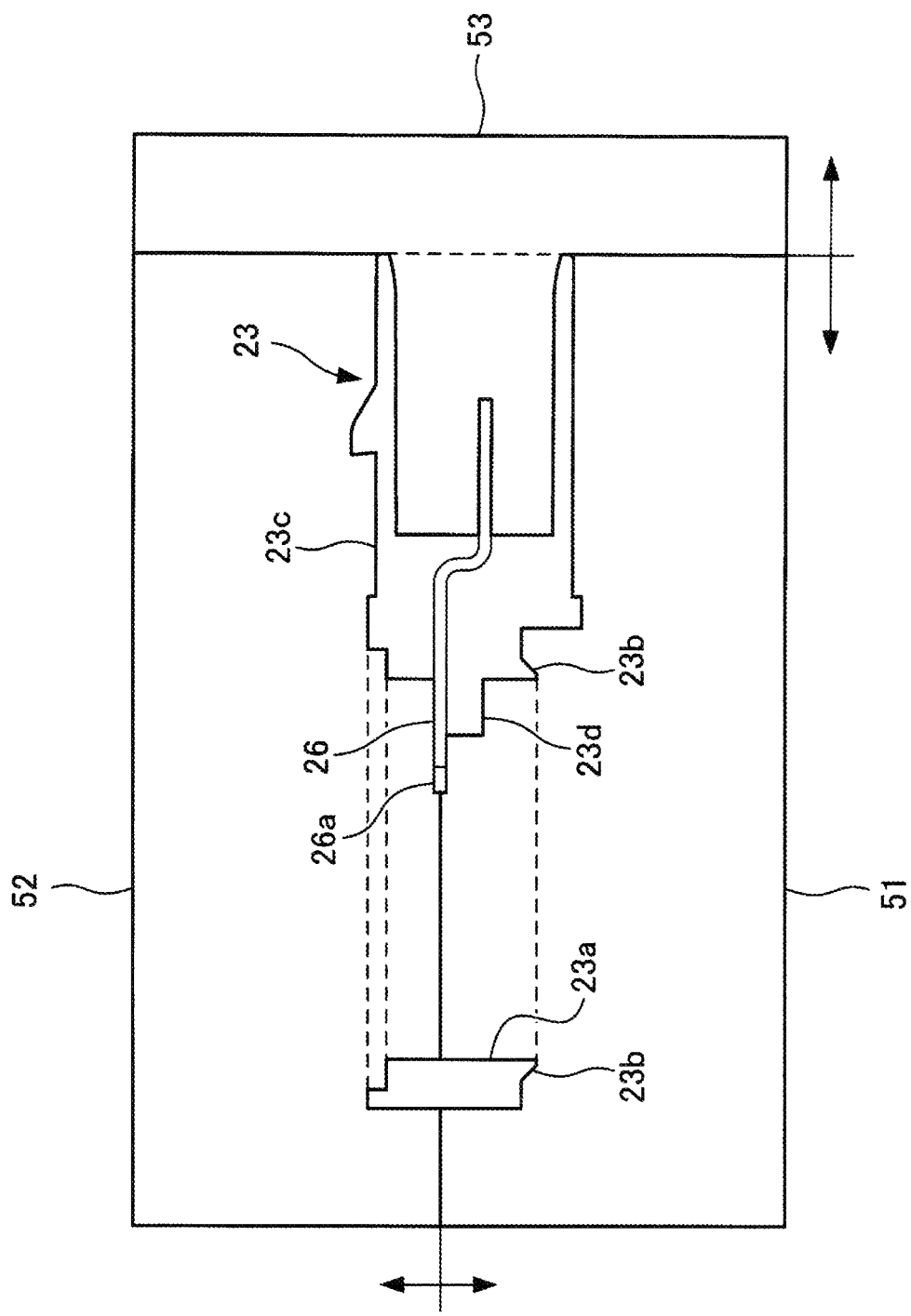
FIG. 6 Sectional view showing molds for insert molding the upper base portion of FIG. 3.

In parallel with or separately from the above-described step of insert-molding the lower base portion 22, insert molding of the upper base portion 23 is performed. As shown in FIG. 6, which is a sectional view showing the insert molding of the upper base portion 23, the insert molding of the upper base portion 23 is performed through use of a first upper portion mold 51, a second upper portion mold 52, and a third upper portion mold 53. The first upper portion mold 51 has an uneven profile formed thereon which corresponds to a lower half of the through-hole 23a, the combining protrusion 23b and the lower surface of the connector portion 23c. The second upper portion mold 52 has an uneven profile formed thereon which corresponds to an upper half of the through-hole 23a and the upper surface of the connector portion 23c. The third upper portion mold 53 has an uneven profile formed thereon which corresponds to the internal shape of the connector portion 23c.

Notably, arrows provided on the left side of the first upper portion mold 51 and the second upper portion mold 52 in FIG. 6 show a parting plane between the first upper portion mold 51 and the second upper portion mold 52; arrows provided on the lower side of the first upper portion mold 51 and the third upper portion mold 53 show a parting plane between the first upper portion mold 51 and the third upper portion mold 53 and a parting plane between the second upper portion mold 52 and the third upper portion mold 53.

Figure 7:
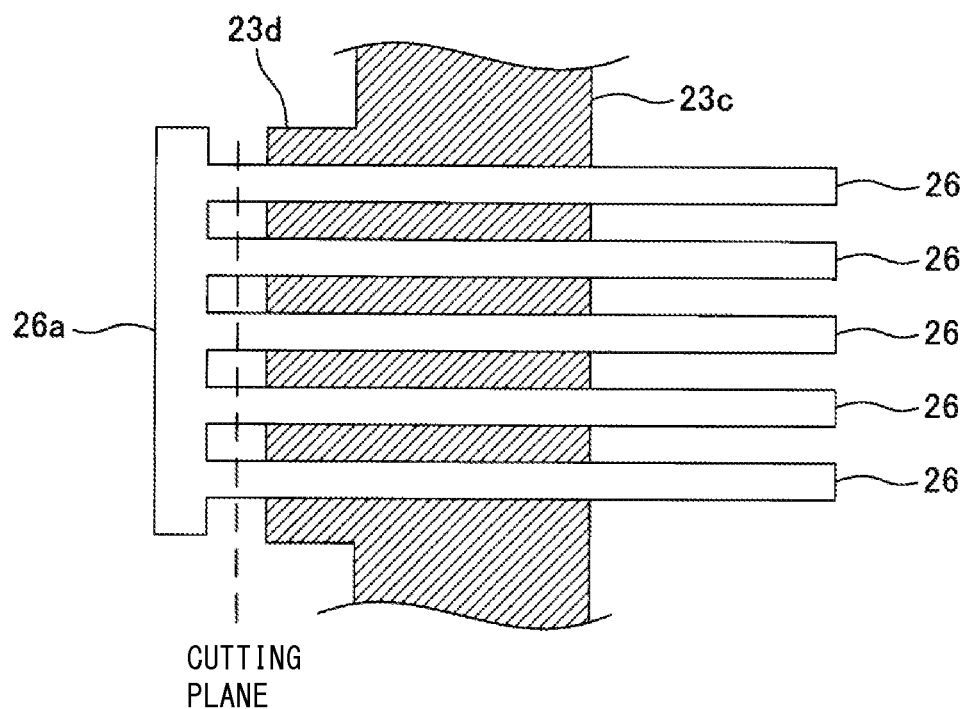
FIG. 7 Schematic view showing the structure of a plurality of terminals united by a connection portion of FIG. 6.

When the upper base portion 23 is insert-molded, as shown in FIGS. 6 and 7, the plurality of terminals 26 united by a connection portion 26a are disposed at a predetermined position in the cavity formed by the first upper portion mold 51, the second upper portion mold 52, and the third upper portion mold 53.

As shown in FIG. 7, the connection portion 26a is a member which is provided at the ends of the plurality of terminals 26 on the side toward the through-hole 23a such that the connection portion 26a extends in a direction perpendicular to the terminals 26. The plurality of terminals 26 are connected by the connection portion 26a for unification. After completion of the insert molding of the upper base portion 23, the connection portion 26a is separated from the terminals 26 through a cutting operation along a cutting plane which is performed by cutting tools inserted into the through-hole 23a through the opposite openings thereof.

When the insert molding of the lower base portion 22 and the upper base portion 23 is completed in the above-described manner, as shown in FIGS. 4(c) and 4(d), the upper base portion 23 is disposed on the lower base portion 22. At that time, the combining protrusion 23b is fitted into the combining groove 22a (see FIG. 1), and the lower base portion 22 and the upper base portion 23 are then fused together and unified, whereby the base portion 21 is obtained. Known fusing methods such as laser fusion, ultrasonic fusion, and thermal fusion may be used, and no particular limitation is imposed on the fusing method.

When the lower base portion 22 and the upper base portion 23 are united, as shown in FIGS. 4(e) and 4(f), the separator 25 is disposed in the space formed by the through-hole 23a and the separator hole 22b. At that time, the rear end portion of the sensor element 12 is inserted into the separator 25, whereby the five electrode terminals of the sensor element 12 are electrically connected to the five conduction members 25a. Simultaneously, the five conduction members 25a are electrically connected to the five terminals 26 of the connector portion 23c (see FIG. 1).

Subsequently, as shown in FIGS. 4(f) and 4(g), the cap portion 24 is disposed at the upper opening of the through-hole 23a, whereby the space which accommodates the separator 25 is sealed. Thus, the assembly of the oxygen sensor 1 is completed.

According to the above-described structure, the base portion 21 is composed of at least the lower base portion 22 which is formed from resin through insert molding to be united with the element assembly 11 including the metallic shell 13, and the upper base portion 23 which is formed from resin through insert molding such that the upper base portion 23 has the connector portion 23c. Through employment of such a structure, it becomes possible to increase the degree of freedom in designing the shape of the base portion 21 formed of resin.

Specifically, when the lower base portion 22 is formed from resin through insert molding, the shape of the element assembly 11 mainly restricts the shape of the lower base portion 22. In the case where the base portion 21 is molded as a single member without diving it, the shape of the element assembly 11 and the position and orientation of the terminals 26 mainly restrict the shape of the lower base portion 22. As compared with such a case, the restriction on the insert molding of the lower base portion 22 decreases, and the degree of freedom in designing the shape of the base portion 21 increases. Similarly, when the upper base portion 23 is formed from resin through insert molding, the position and orientation of the terminals 26 mainly restrict the shape of the upper base portion 23. Therefore, as compared with the case where the base portion 21 is insert-molded as a single member without diving it, the above-mentioned restriction decreases, and the degree of freedom in designing the shape of the base portion 21 increases.

Furthermore, when the lower base portion 22 and the upper base portion 23 are united after being insert-molded separately, the direction of the upper base portion 23 (the direction of the connector portion 23c) in the circumferential direction in relation to the lower base portion 22 can be set to a predetermined direction. Namely, the direction of the connector portion 23c can be set freely irrespective of the shapes of the lower base portion 22, the element assembly 11, etc.

Moreover, as compared with the case where the base portion 21 is insert-molded as a single member without diving it, the lower base portion 22 and the upper base portion 23 can have a simple shape, in particular, a shape which is symmetric with respect to an axis or a line. Therefore, it become easier to suppress deformation of the lower base portion 22 and the upper base portion 23 caused by shrinkage of resin after completion of insert molding.

Since the shapes of the lower base portion 22 and the upper base portion 23 can be made relatively simple, the shapes of molds used for insert-molding the lower base portion 22 and the upper base portion 23 can be made simple. Therefore, the manufacturing cost of the molds can be lowered, and the lives of the molds can be extended. As a result, the manufacturing cost of the oxygen sensor 1 can be lowered.

Also, since the end portions of the plurality of terminals 26 on the side toward the separator 25 project inward from the wall surface of the through-hole 23a, it becomes easier to suppress deterioration of the accuracy in positioning the terminals 26 in relation to one another. Specifically, the required operation is merely disposing the plurality of terminals 26 united by the connection portion 26a in the first upper portion mold 51, the second upper portion mold 52, and the third upper portion mold 53. Therefore, as compared with the case where the plurality of terminals 26 are disposed one by one in the first upper portion mold 51, the second upper portion mold 52, and the third upper portion mold 53, it becomes easier to suppress deterioration of the accuracy in positioning the terminals 26. Also, the work required for disposing the plurality of terminals 26 can be eliminated.

Also, since the connection portion 26a and the end portions of the plurality of terminals 26 on the side toward the separator 25 project toward the interior of the through-hole 23a of the upper base portion 23, the connection portion 26a can be readily separated from the terminals 26. Namely, since a pair of cutting tools for separating the connection portion 26a from the terminals 26 can be inserted into the through-hole 23a through the opposite openings thereof, the operation of nipping and cutting the portions between the connection portion 26a and the terminals 26 is easy as compared with the case where the connection portion 26a projects toward the interior of a hole which is closed at one end thereof.

By means of forming the recess 22c in the upper part 22U of the lower base portion 22, the amount of resin used for forming the lower base portion 22 can be reduced without deteriorating the shape accuracy of the base portion 21. At the same time, the weight of the oxygen sensor 1 can be reduced. That is, since a connector portion 23c which greatly impairs axis symmetry or plane symmetry is not provided on the lower base portion 22, the shrinkage of resin after completion of molding is less likely to cause deformation of the lower base portion 22. In particular, even when the recess 22c is provided at a position where the recess 22c overlaps the connector portion 23c, the lower base portion 22 hardly deforms. Therefore, the recess 22c can be easily provided.

[Second Embodiment]

Figure 8:
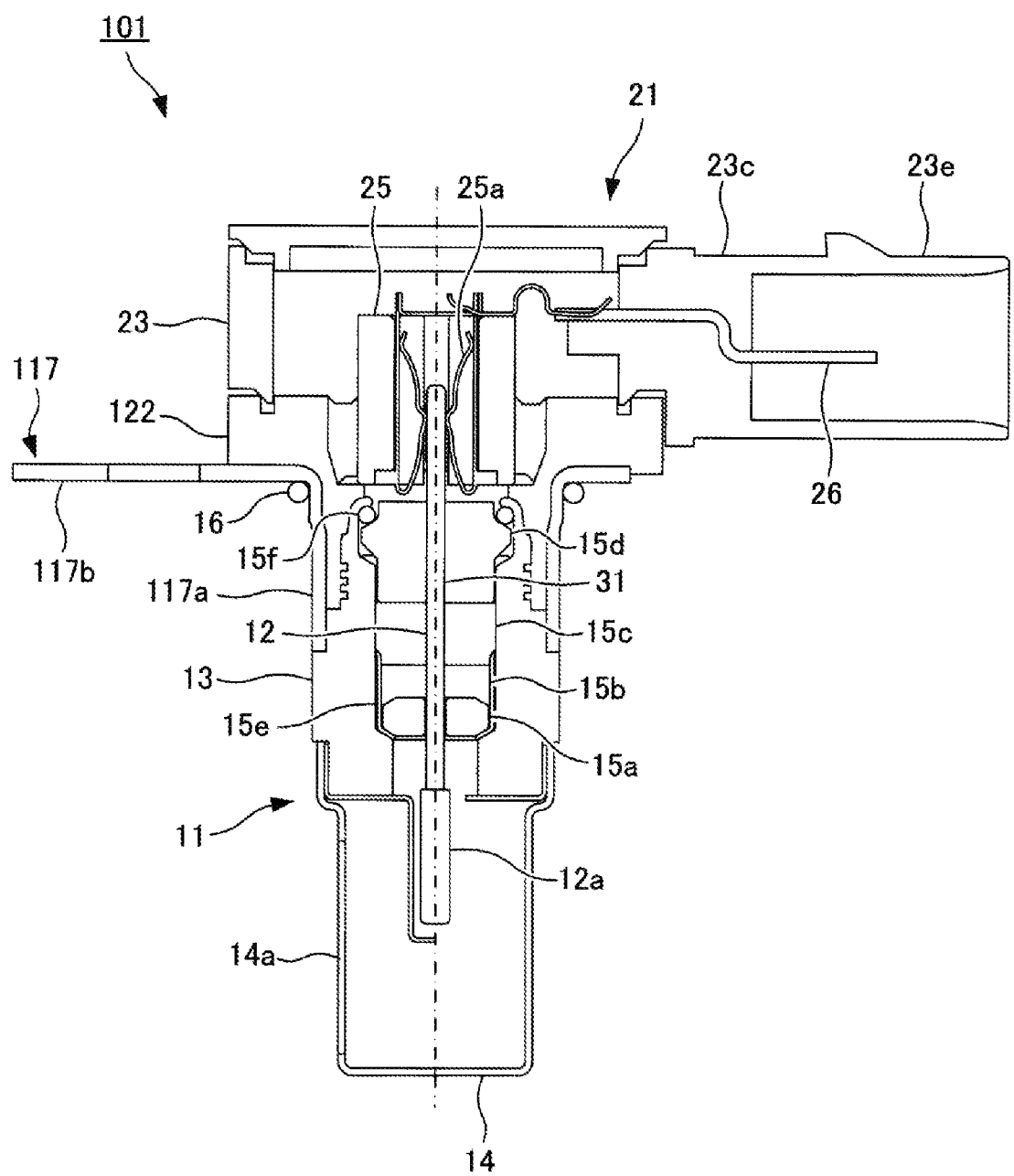
FIG. 8 Sectional view schematically showing the structure of an oxygen sensor according to a second embodiment of the present invention.

Next, a second embodiment of the present invention will be described with reference to FIGS. 8 to 12. Although the oxygen sensor of the present embodiment has a basic structure identical to that of the oxygen sensor of the first embodiment, the oxygen sensor of the present embodiment differs from the oxygen sensor of the first embodiment in that a flange portion is provided. Therefore, in the present embodiment, only the point different from the first embodiment (i.e., the flange portion) will be described with reference to FIGS. 8 to 12, and description of portions identical to those of the first embodiment is omitted. FIG. 8 is a sectional view schematically showing the structure of an oxygen sensor 101 according to the present embodiment.

As shown in FIG. 8, the oxygen sensor 101 of the present embodiment is mainly composed of the element assembly 11 which includes a flange portion 117, and the base portion 21 which includes a lower base portion (first base portion) 122.

The flange portion 117 is a component which is formed of metal and which is used when the oxygen sensor 101 is fixed to the intake pipe. The flange portion 117 is mainly composed of a cylindrical tube part 117a and a pair of plate-like flange pieces 117b. An end of the tube part 117a on the side toward the metallic shell 13 is fixed to the metallic shell 13. The pair of flange pieces 117b extend from an end of the tube part 117a on the side toward the base portion 21 in a direction (the left-right direction in FIG. 8) intersecting (more preferably, perpendicular to) the insertion direction of the oxygen sensor 101 (the vertical direction in FIG. 8).

Notably, in FIG. 8, the flange portion 117 is depicted in a state in which one of the flange pieces 117b extends in a direction toward which the gas introduction hole 14a is open. However, the direction in which the flange pieces 117b extend is not limited to the direction shown in FIG. 8, and may be set freely. For example, the direction in which the flange pieces 117b extend may be rotated by 90°; namely, the flange pieces 117b may extend in a direction perpendicular to the direction toward which the gas introduction hole 14a is open.

Figure 9:
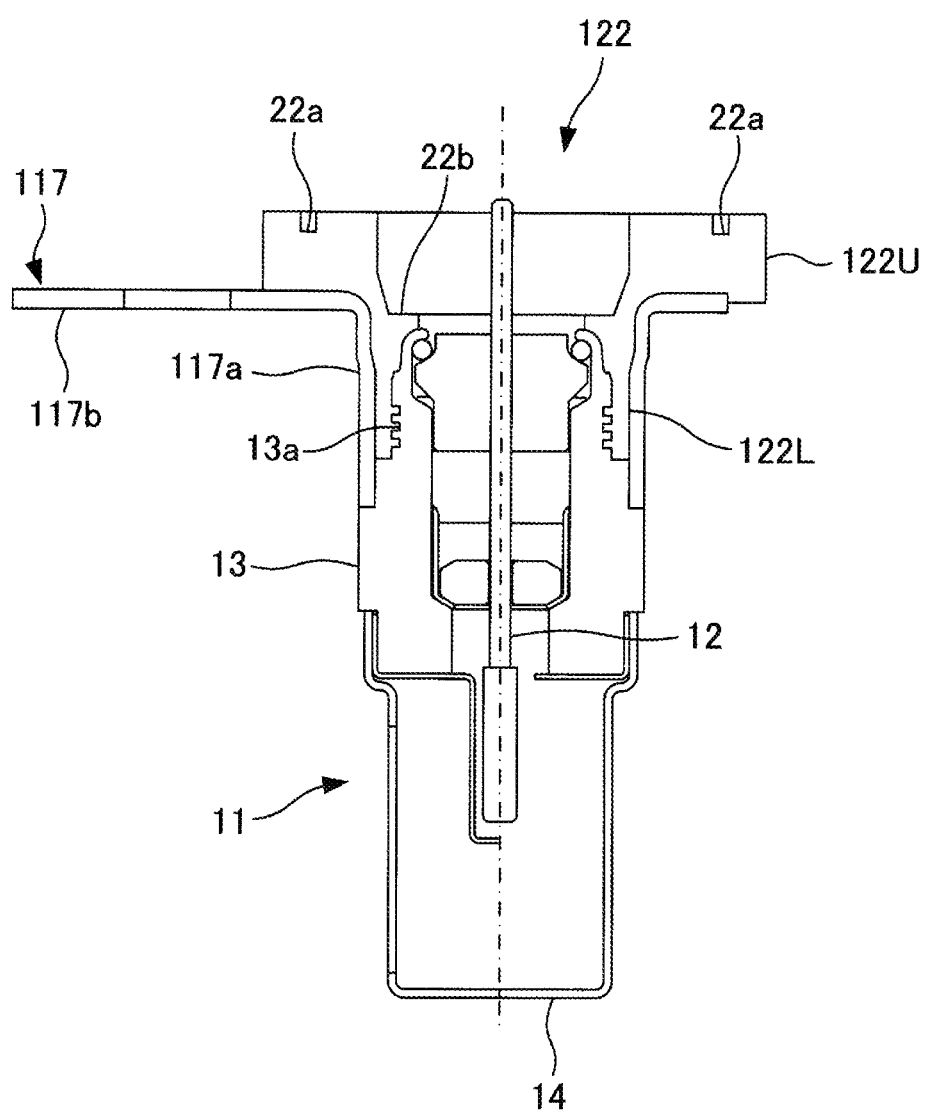
FIG. 9 Partial sectional view showing the structure of a lower base portion of FIG. 8.

As shown in FIG. 9, which is a partial sectional view showing the structure of the lower base portion 122, a lower part 122L of the lower base portion 122 is formed into a cylindrical tubular shape so as to fill the space between the outer circumference of the metallic shell 13 and the inner circumference of the tube part 117a of the flange portion 117. An upper part 122U of the lower base portion 122 is formed into the shape of a plate which is located above the flange pieces 117b of the flange portion 117 and projects outward from the lower part 122L in the radial direction.

Here, the steps of assembling the oxygen sensor 101 will be briefly described with reference to FIGS. 10(a) to 10(g), which are perspective views showing the steps of assembling the oxygen sensor 101.

First, as shown in FIG. 10(a), the element assembly 11, which is composed of the sensor element 12, the metallic shell 13, the external protector 14, the ceramic ring 15a, the first talc ring 15b, the second talc ring 15c, the sleeve 15d, and the flange portion 117 is prepared (see FIG. 8). Notably, a known fixing method such as welding may be used to fix the flange portion 117 to the metallic shell 13.

Figure 11:
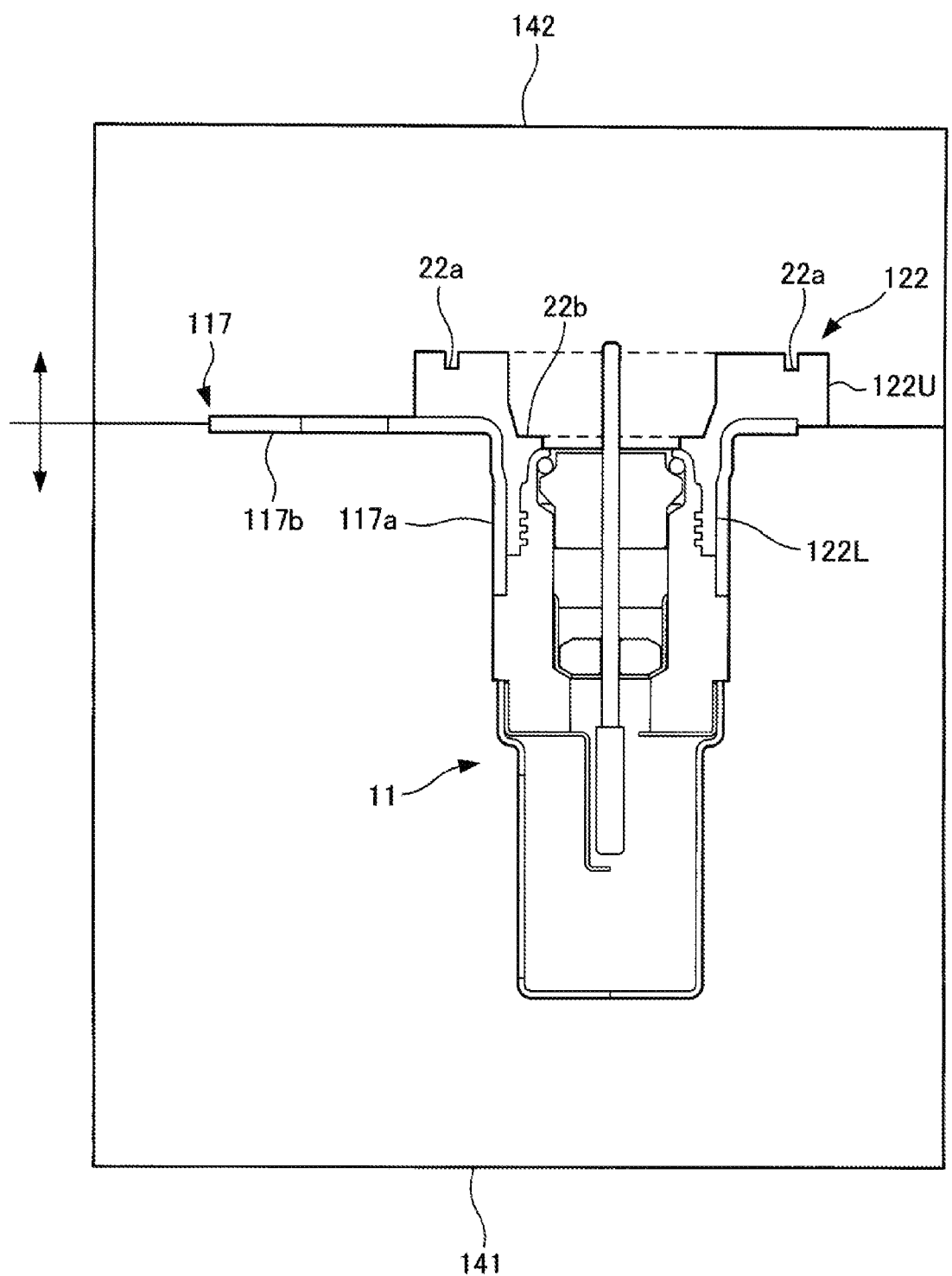
FIG. 11 Sectional view showing insert molding of the lower base portion of FIG. 8.

Subsequently, as shown in FIG. 10(b), the lower base portion 122 is insert-molded on the element assembly 11. As shown in FIG. 11, which is a sectional view showing the insert molding of the lower base portion 122, the insert molding is performed through use of a first lower portion mold 141 and a second lower portion mold 142. The first lower portion mold 141 has a convex profile or shape formed thereon which corresponds to the element assembly 11. The second lower portion mold 142 has an uneven profile formed thereon which corresponds to the side and upper surfaces of the upper part 122U of the lower base portion 122. More specifically, concaves and convexes corresponding to the combing groove 22a, the separator hole 22b, etc. are formed.

Notably, arrows provided on the right side of the first lower portion mold 141 and the second lower portion mold 142 in FIG. 11 show a parting plane between the first lower portion mold 141 and the second lower portion mold 142. Namely, the parting plane between the first lower portion mold 141 and the second lower portion mold 142 is disposed such that it coincides with the flange pieces 117b of the flange portion 117.

The remaining steps of assembling the oxygen sensor 101, such as the step of insert-molding the upper base portion 23 and the step of stacking the lower base portion 122 and the upper base portion 23, are identical to those of the first embodiment. Therefore, the details of the remaining steps are shown in FIGS. 10(c) to 10(g), and description of the remaining steps is omitted.

According to the above-described structure, the lower base portion 122 is insert-molded to be united with the element assembly 11 including the flange portion 117 through use of the first lower portion mold 141 and the second lower portion mold 142, the parting plane of which coincides with the flange pieces 117b of the flange portion 117. In the case where a restriction is imposed on the position of the parting plane of the molds, the oxygen sensor 101 of the present embodiment can simplify the shape of the molds as compared with the case where the base portion 21 is formed as a single member without dividing it (see FIG. 12), because the connector portion 23c is not provided on the lower base portion 122 which is molded integrally with the element assembly 11 including the flange portion 117.

Figure 12:
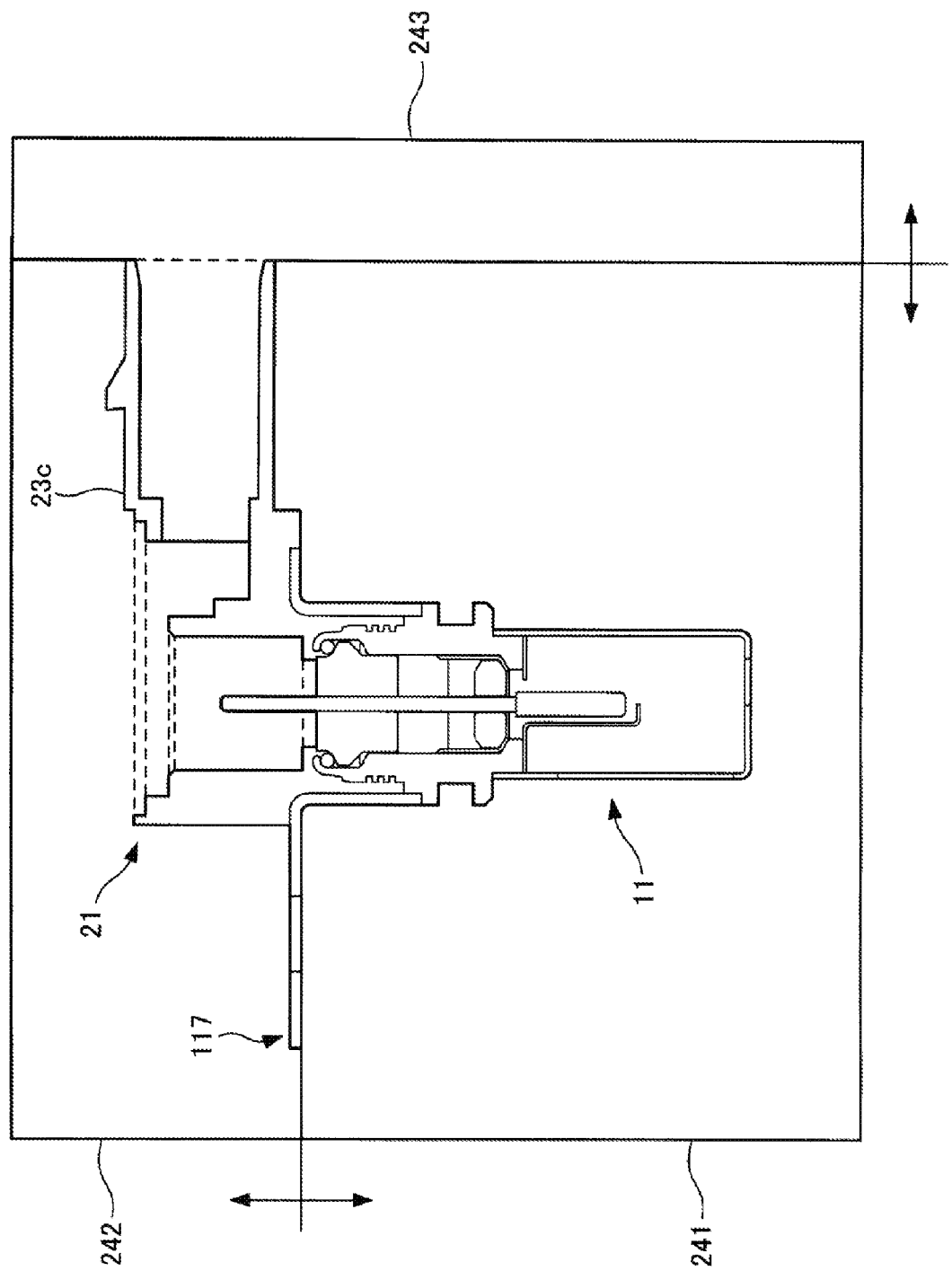
FIG. 12 Sectional view showing insert molding of the base portion of a conventional oxygen sensor.

Molds which are used to mold the base portion 21 as a single member without dividing it will be described with reference to FIG. 12. Insert molding is performed through use of a first mold 241, a second mod 242, and a third mold 243. The first mold 241 has a concave shape or profile formed thereon which corresponds to the element assembly 11 and the lower surface of the connector portion 23c. The second mold 242 has an uneven profile formed thereon which corresponds to the side and upper surface of the upper part of the base portion 21 and the upper surface of the connector portion 23c. The third mold 243 has an uneven profile formed thereon which corresponds to the internal shape of the connector portion 23c.

[Third Embodiment]

Next, a third embodiment of the present invention will be described with reference to FIGS. 13 to 15.

Although the oxygen sensor of the present embodiment has a basic structure identical to that of the oxygen sensor of the first embodiment, the oxygen sensor of the present embodiment differs from the oxygen sensor of the first embodiment in that at least the first base portion is formed of metal. Therefore, in the present embodiment, only the point different from the first embodiment will be described with reference to FIGS. 13 to 15, and description of portions identical to those of the first embodiment is omitted.

Figure 13:
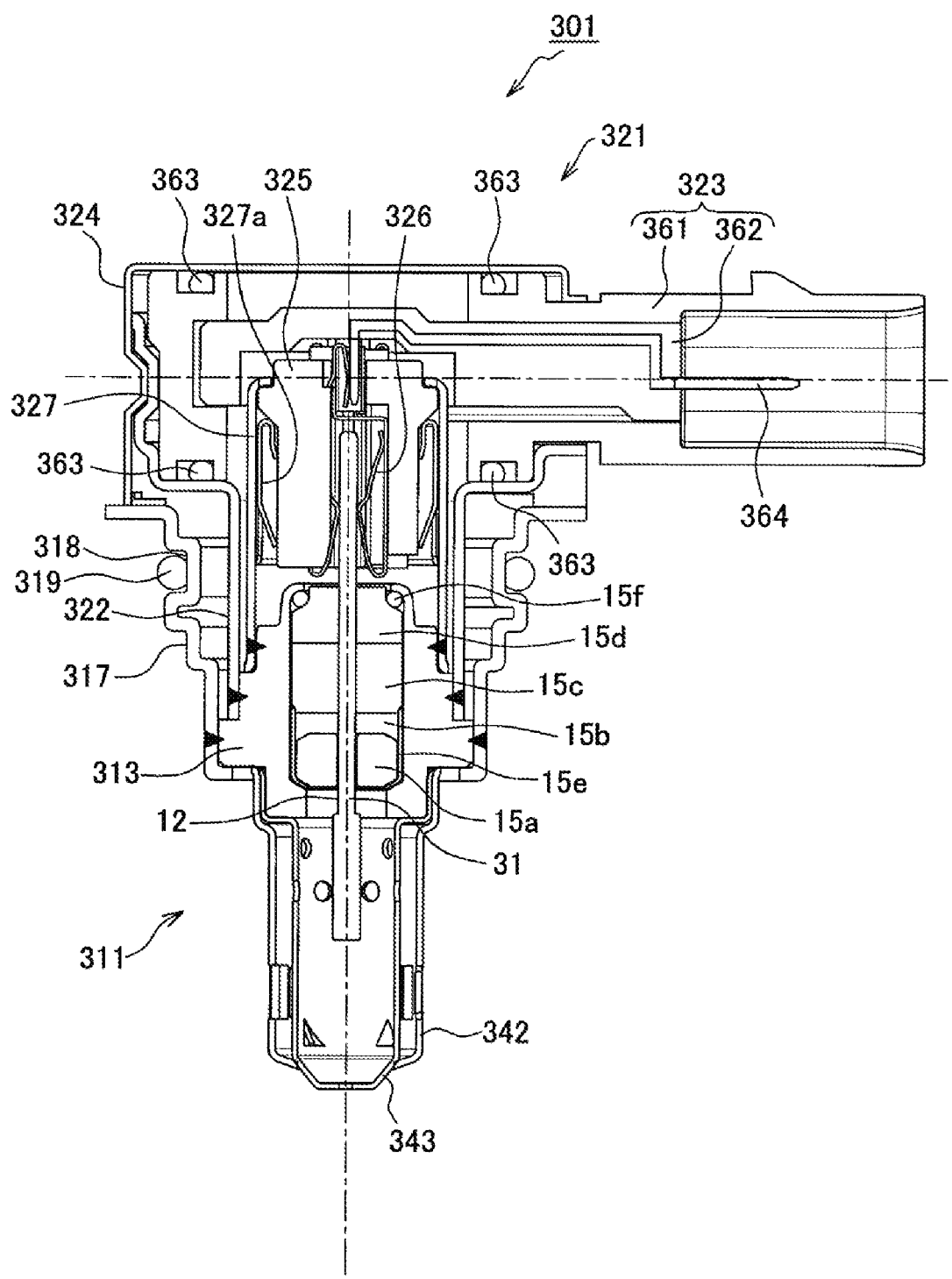
FIG. 13 Sectional view schematically showing the structure of an oxygen sensor according to a third embodiment of the present invention.
Figure 14:
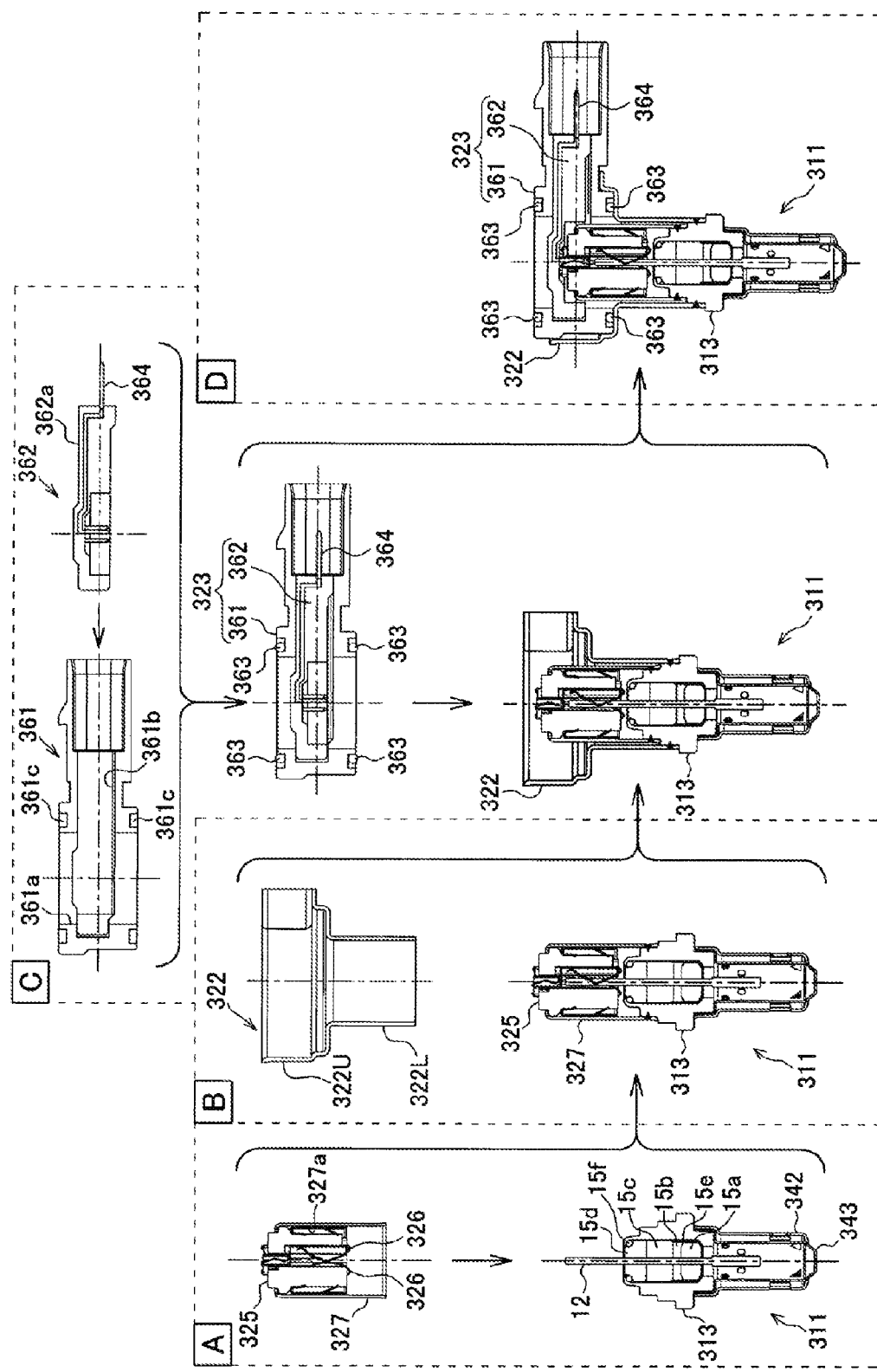
FIG. 14 Explanatory views showing steps A to D of the steps of assembling the oxygen sensor of FIG. 13.

FIG. 13 is a sectional view schematically showing the structure of an oxygen sensor 301 according to the present embodiment, and FIGS. 14 and 15 are explanatory views showing the steps of assembling the oxygen sensor 301.

As shown in FIG. 13, the oxygen sensor 301 of the present embodiment is mainly composed of an element assembly 311 which includes a mounting member 317, and a base portion 321 which includes a lower base portion (first base portion) 322.

The element assembly 311 is mainly composed of the sensor element 12; a metallic shell (housing) 313 which accommodates and holds the sensor element 12; the ceramic ring 15a; the first talc ring 15b; the second talc ring 15c; the sleeve 15*d*, the metal cup 15*e*, the packing 15*f*, an external protector 342, an internal protector 343, and a mounting member 317.

The mounting member 317 of the element assembly 311 is a metallic component which is used for fixing the oxygen sensor 301 to the intake pipe. The mounting member 317 has a tubular shape such that the metallic shell 313 can be disposed inside the mounting member 317, and its forward end portion is fixed to the metallic shell 313 by welding. The mounting member 317 has a groove 318 on its outer circumferential surface (see the step F of FIG. 15), and an annular packing 319 is disposed in the groove 318. Also, the mounting member 317 has a mounting hole formed in a portion thereof which extends radially outward from the rear end of the mounting member 317. This mounting hole is provided for mounting the oxygen sensor 301 to a sensor attachment location (the intake pipe or the like) by, for example, screwing with a bolt or the like.

The external protector 342 and the internal protector 343 are members formed of metal (e.g., stainless steel) and having a plurality of holes, and are attached (by welding or the like) to the outer circumference of a forward end portion (a lower portion in FIG. 13) of the metallic shell 313 such that the external protector 342 and the internal protector 343 cover the projecting portion of the sensor element 12.

As shown in FIG. 13, the base portion 321, which is to be disposed outside the intake pipe, is mainly composed of the lower base portion (first base portion) 322, an upper base portion (second base portion) 323, and a cap portion 324. A separator (relay portion) 325 and a tubular support member 327 for supporting the separator 325 are disposed within the base portion 321. The separator (relay portion) 325 establishes electrical communication between a plurality of metallic terminals 364 to be described later and the sensor element 12. Notably, the support member 327 has a tubular member 327*a* provided therein. The tubular member 327*a* is configured to change its inner diameter upon elastic deformation thereof whereby the tubular member 327*a* can hold the separator 325 within the support member 327.

In the present embodiment, the lower base portion 322 and the cap portion 324 are formed of a metallic material (SUS304 or the like), and the upper base portion 323 is formed of polyphenylene sulfide resin.

The lower base portion 322 constitutes a portion (a lower portion in FIG. 13) of the base portion 321 located on the side toward the metallic shell 313 and the sensor element 12, and is formed of stainless steel (SUS304 or the like). As shown in the step B of FIG. 14, a lower part 322L of the lower base portion 322 is formed into the shape of a cylindrical tube which can accommodate a rear end portion (an upper end portion in FIG. 14) of the metallic shell 313. An upper part 322U of the lower base portion 322 is formed into a shape for accommodating a portion of the upper base portion 323.

The upper base portion 323, which constitutes a portion (an upper portion in FIG. 13) of the base portion 321 located away from the metallic shell 313 and the sensor element 12, is a component which extends in a direction (the left-right direction in FIG. 13) intersecting (more preferably, perpendicular to) the insertion direction of the oxygen sensor 301 (the vertical direction in FIG. 13). As shown in the step C of FIG. 14, the upper base portion 323 is mainly composed of an outer member 361 supported by the lower base portion 322, and a connector member 362 accommodated in the outer member 361.

The outer member 361 has a through-hole 361*a*, a connector accommodation portion 361*b*, and O-ring disposing portions 361*c*.

The through-hole 361*a* is a hole which is formed in a part of the upper base portion 323 facing the lower base portion 322 such that the hole extends through that part in the insertion direction of the oxygen sensor 301; i.e., in a direction in which the sensor element 12 extends.

The connector accommodation portion 361*b* is a space for accommodating the connector member 362, and communicates with the through-hole 361*a*.

The O-ring disposing portions 361*c* are grooves in which O-rings 363 are disposed, and are formed on the forward end and rear end sides, respectively, of the outer member 361. The O-rings 363 are members formed from elastic resin such as rubber into a ring-like shape, and have a circular cross section. When disposed in the O-ring disposing portions 361*c*, the O-rings 363 enhance the airtightness between the upper base portion 323 (outer member 361) and the lower base portion 322, and also enhance the airtightness between the upper base portion 323 (outer member 361) and the cap portion 324.

The connector member 362 serves as a connection portion through which a measurement signal from the sensor element 12 is output to a control section (not shown) disposed externally of the oxygen sensor 301, and through which electric power supplied to the heater 31 is input. The connector member 362 is mainly composed of the plurality of metallic terminals 364 which are connected to a plurality of conduction members 326, and a tubular portion 362*a* which extends to surround the metallic terminals 364.

The upper base portion 323 is formed by disposing the connector member 362 into the connector accommodation portion 361*b* of the outer member 361.

As a result of a portion of the upper base portion 323 being disposed in the interior of the upper part 322U of the lower base portion 322, the plurality of metallic terminals 364 are electrically connected to the plurality of conduction members 326. Notably, the plurality of conduction members 326 are disposed inside the separator 325 and are electrically connected to the sensor element 12 and the heater 31. Thus, the plurality of metallic terminals 364 are electrically connected to the sensor element 12 and the heater 31.

As shown in the step E of FIG. 15, the cap portion 324 is mainly composed of an upper surface portion 324*a* which covers a portion of the upper surface of the upper base portion 323, and a side surface portion 324*b* which covers a portion of the side surface of the upper base portion 323. The side surface portion 324*b* has an opening 324*c* having a size which enables the upper base portion 323 to be inserted into the opening 324*c*.

The cap portion 324 covers the through-hole 361*a* by its upper surface portion 324*a* so as to close the space in which the rear end of the sensor element 12 and the separator 325 are disposed. Thus, the cap portion 324 prevents entry of water or the like into this space.

Here, the steps of assembling the oxygen sensor 301 will be briefly described with reference to FIGS. 14 and 15, which are explanatory views showing the steps of assembling the oxygen sensor 301.

First, as shown in the step A of FIG. 14, an element assembly 311 is prepared. The element assembly 311 is composed of the sensor element 12, the metallic shell 313, the ceramic ring 15*a*, the first talc ring 15*b*, the second talc ring 15*c*, the sleeve 15*d*, the metal cup 15*e*, the packing 15*f*, the external protector 342, and the internal protector 343.

The support member 327, which accommodates the separator 325 and the plurality of conduction members 326, is assembled to the element assembly 311, and the support member 327 and the element assembly 311 (specifically, the metallic shell 313) are fixed together by welding. As a result, the plurality of conduction members 326 are electrically connected to the sensor element 12 and the heater 31. Notably, the support member 327 includes the tubular member 327a which is configured to change its inner diameter upon elastic deformation thereof whereby the tubular member 327a can hold the separator 325 within the support member 327.

Next, as shown in the step B of FIG. 14, the lower base portion 322 is assembled to the element assembly 311 to which the support member 327 has been fixed, and the lower base portion 322 and the element assembly 311 (specifically, the metallic shell 313) are fixed together by welding.

Next, as shown in the step C of FIG. 14, the upper base portion 323 is formed by disposing the connector member 362 in the connector accommodation portion 361b of the outer member 361.

Subsequently, the upper base portion 323 is assembled to the element assembly 311 to which the lower base portion 322 has been fixed. At that time, one O-ring 363 is disposed in the lower O-ring disposing portion 361c, whereby the O-ring 363 is disposed between the lower base portion 322 and the upper base portion 323.

As a result, as shown in the step D of FIG. 14, a portion of the upper base portion 323 is disposed inside the upper part 322U of the lower base portion 322, and the plurality of metallic terminals 364 are electrically connected to the plurality of conduction members 326.

Next, as shown in the step E of FIG. 15, the cap portion 324 is assembled to the element assembly 311 to which the lower base portion 322 has been fixed and the upper base portion 323 has been assembled. At that time, the other O-ring 363 is disposed in the upper O-ring disposing portion 361c, whereby the O-ring 363 is disposed between the cap portion 324 and the upper base portion 323.

As a result, the through-hole 361a is covered by the upper surface portion 324a of the cap portion 324. Thus, the space in which the rear end of the sensor element 12 and the separator 325 are disposed becomes a closed space, whereby entry of water or the like into that space is prevented. Also, after being assembled to the lower base portion 322, the cap portion 324 is crimped in the radial direction and is fixed.

Next, as shown in the step F of FIG. 15, the mounting member 317 is assembled to the element assembly 311 to which the cap portion 324 has been assembled. At that time, the mounting member 317 is assembled to the forward end side (the lower side in FIG. 15) of the element assembly 311, and these members are fixed together by welding.

As a result, the oxygen sensor 301 is completed as shown in the step G of FIG. 15

In the oxygen sensor 301 configured as described above, the lower base portion 322 is a member formed of metal (stainless steel). Therefore, as compared with a member formed of resin, the member which constitutes the lower base portion 322 is excellent in heat resistance, which enables the oxygen senor to be used in a high temperature environment.

Notably, the present embodiment, the sensor element 12 corresponds to an example of the sensor element in claims; and the metallic shell 313 (housing 313) corresponds to an example of the housing in claims. The base portion 321 corresponds to an example of the base portion in claims; the lower base portion 322 (first base portion 322) corresponds to an example of the first base portion in claims; and the upper base portion 323 (second base portion 323) corresponds to an example of the second base portion in claims. The plurality of metallic terminals 364 correspond to an example of the plurality of terminals in claims; the connector member 362 corresponds to an example of the connector portion in claims; the through-hole 361a corresponds to an example of the through-hole in claims; and the separator 325 (relay portion) and the conduction members 326 correspond to an example of the relay portion in claims.

Although the embodiments of the present invention have been described, the present invention is not limited to the above-described embodiments, and may be practiced in various ways without departing from the scope of the present invention.

For example, in the case where the lower base portion 322 is formed of a metallic material, the material is not limited to SUS304, and the lower base portion 322 may be formed of any of other metallic materials. By forming the lower base portion through use of a metallic material which is excellent in corrosion resistance and heat resistance, the corrosion resistance and heat resistance of the gas sensor (oxygen sensor) can be improved.

DESCRIPTION OF REFERENCE NUMERALS 1, 101, 301: oxygen sensor (gas sensor)
12: sensor element
13, 313: metallic shell (housing)
14: external protector (housing)
21, 321: base portion
22, 122, 322: lower base portion (first base portion)
22c: recess (concave portion)
22U: upper part
22L, 122L: lower part
23, 323: upper base portion (second base portion)
23a, 361a: through-hole
26: plurality of terminals
25, 325 separator (relay portion)
26a: connection portion
117: flange portion
141: first lower portion mold
142: second lower portion mold

The invention claimed is:

1. A gas sensor comprising a sensor element which measures the concentration of a specific gas component contained in gas flowing through a flow passage provided in an internal combustion engine, a housing which accommodates and holds the sensor element and which is inserted into the flow passage, and a base portion which is attached to the housing and which is disposed outside the flow passage, the gas sensor being characterized in that the base portion includes:
 a first base portion which is a portion of the base portion located on the side toward the housing; and
 a second base portion which is molded separately from the first base portion, which is a portion of the base portion located opposite the housing, and which has a connector portion in which a plurality of terminals which are to be connected electrically to the sensor element are disposed such that they extend in a direction intersecting an insertion direction of the sensor element,
 wherein the first base portion is formed of metal, and the first base portion and the housing are fixed together by welding,
 a sleeve and a talc ring are accommodated in the housing, and the sleeve is disposed so as to press the talc ring toward a lower end side of the gas sensor in cooperation with the housing, and
 an upper end of the housing is deformed inward in a radial direction, the radial direction being perpendicular to the insertion direction of the sensor element.

2. A gas sensor as claimed in claim 1, wherein the second base portion is molded through use of resin.

3. A gas sensor as claimed in claim 1, wherein
the second base portion has a through-hole for accommodating a relay portion which electrically connects the sensor element and the plurality of terminals;
the plurality of terminals are molded integrally with the second base portion in a state in which the terminals are united by a connection portion at their end portions on the side toward the relay portion and in a state in which the end portions on the side toward the relay portion project toward the interior of the through-hole; and
subsequently, the connection portion is cut from the plurality of terminals projecting from the wall surface of the through-hole toward the interior thereof, whereby the plurality of terminals are disposed inside the second base portion.

4. A gas sensor as claimed in claim 1, wherein
the first base portion includes a lower part which is a portion on the side toward the housing and which extends in a direction in which the housing extends, and a plate-shaped upper part which is a portion on the side toward the second base portion and which extends in a direction in which the plurality of terminals extend; and
a concave portion is formed on a surface of the upper part located on the side toward the housing.

* * * * *